(12) United States Patent
Heaton et al.

(10) Patent No.: US 6,200,288 B1
(45) Date of Patent: Mar. 13, 2001

(54) EVERTING TOROID DEVICE FOR INSERTION INTO A BODY CAVITY

(75) Inventors: Jeremy P. W. Heaton, Gananoque; Michael A. Adams; James D. Banting, both of Kingston, all of (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/239,950

(22) Filed: Jan. 29, 1999

Related U.S. Application Data (63) Continuation-in-part of application No. 08/917,556, filed on Aug. 26, 1997, now Pat. No. 5,954,688, and a continuation of application No. PCT/CA98/00800, filed on Aug. 26, 1998.

(51) Int. Cl.[7] .......................... A61M 31/00; A61M 5/315; A61M 35/00
(52) U.S. Cl. ............................... 604/59; 604/57; 604/48; 604/311; 604/514; 604/218
(58) Field of Search .................................. 604/48, 68, 96, 604/514, 70, 73, 57–60, 105–107, 311, 218; 222/92, 206, 499, 501, 505, 527

(56) References Cited

U.S. PATENT DOCUMENTS

| | | |
|---|---|---|
| 268,805 | 12/1882 | Knight . |
| 602,010 | 4/1898 | Hoenig . |
| 634,982 | 10/1899 | Johnson . |
| 643,867 | 2/1900 | Vilbiss . |
| 683,589 | 10/1901 | Barry . |
| 719,586 | 2/1903 | Hasbrouck . |
| 742,634 | 10/1903 | Hall . |
| 1,628,843 | 5/1927 | Horton . |
| 1,642,950 | 9/1927 | Haas . |
| 1,685,280 | 9/1928 | Findley . |
| 3,168,092 | 2/1965 | Silverman . |
| 3,500,819 | 3/1970 | Silverman . |
| 3,589,356 | * 6/1971 | Silverman . |
| 3,669,099 | * 6/1972 | Silverman . |
| 4,254,774 | 3/1981 | Boretos . |
| 4,776,848 | 10/1988 | Solazzo . |
| 4,801,444 | 1/1989 | Kravchenko . |
| 4,801,587 | 1/1989 | Voss et al. . |
| 4,900,303 | 2/1990 | Lemelson . |
| 4,994,066 | 2/1991 | Voss . |
| 5,045,070 | 9/1991 | Grodecki et al. . |
| 5,100,383 | 3/1992 | Lichtenstein . |
| 5,171,305 | 12/1992 | Schickling et al. . |
| 5,190,192 | 3/1993 | Lina et al. . |
| 5,234,135 | 8/1993 | LaFosse et al. . |
| 5,328,099 | 7/1994 | Petit et al. . |
| 5,330,446 | 7/1994 | Weldon et al. . |

(List continued on next page.)

FOREIGN PATENT DOCUMENTS

| | | |
|---|---|---|
| 3329176 | 11/1984 | (DE) . |
| 0357581 | 3/1990 | (EP) . |
| 0432199 | 6/1991 | (EP) . |
| 88/01924 | 3/1988 | (WO) . |

Primary Examiner—Dennis Ruhl
(74) Attorney, Agent, or Firm—Stephen J. Scribner; Carol Miernicki Steeg; Richard J. Hicks (57) ABSTRACT

An everting toroid for use in delivering a powdered, fluid, or aerosolized pharmaceutical composition, or other composition, to an internal body cavity, such as the urethra, or other cavity, is contained within a tubular housing and may be extended therefrom and retracted back into the tubular housing. The composition may be distributed on the surface of the everting toroid when made from an impermeable membrane, contained within the toroid when made from a permeable membrane, or may be injected through the lumen thereof via an aerosol wand which releases the composition as the toroid and/or wand are withdrawn from the cavity.

20 Claims, 5 Drawing Sheets

U.S. PATENT DOCUMENTS

| | | |
|---|---|---|
| 5,337,923 | 8/1994 | Lugez et al. . |
| 5,368,016 | 11/1994 | Henry . |
| 5,374,247 | 12/1994 | Lowery et al. . |
| 5,443,447 * | 8/1995 | Kassis .................................. 604/96 |
| 5,453,445 | 9/1995 | Henry . |
| 5,474,535 | 12/1995 | Place et al. . |
| 5,482,039 | 1/1996 | Place . |
| 5,489,435 | 2/1996 | Ratcliff . |
| 5,511,698 | 4/1996 | Solignac . |
| 5,534,242 | 7/1996 | Henry . |
| 5,589,156 | 12/1996 | Henry . |
| 5,593,661 | 1/1997 | Henry . |
| 5,954,688 * | 9/1999 | Adams et al. ......................... 604/59 |

* cited by examiner

EVERTING TOROID DEVICE FOR INSERTION INTO A BODY CAVITY

CROSS REFERENCE TO RELATED APPLICATIONS

This application is a continuation-in-part of U.S. patent application Ser. No. 08/917,566 filed Aug. 26, 1997, now U.S. Pat. No. 5,954,688 the contents of which incorporated by reference in their entirety. This application is also a U.S. continuation of PCT International Application No. PCT/CA98/00800, filed Aug. 26, 1998.

FIELD OF THE INVENTION

This invention relates to an everting device for delivering a drug, absorbent, or other preparation in powder, liquid, gel, cream, or aerosol form to an internal body cavity or other cavity. More particularly this invention relates to an everting toroid device and methods for delivering a drug or the like to the will lumen or interior wall, vagina, or other lumen or internal mucosal or absorptive so. Application to inmate or artificial surfaces, e.g., inner tubular walls and the like, is also contemplated.

BACKGROUND OF INVENTION

Everting sleeve devices for probing internal body cavities, for delivering drugs in powder form to the surfaces of those cavities, and for taking samples from within the cavity are well known in the medical arts. Attention is directed to U.S. Pat. Nos. 3,168,092 issued Feb. 2, 1965, No. 3,500,819 issued Mar. 17, 1970 and No. 3,589,356 issued Jun. 29, 1971, all to Daniel Silverman, which are typical of the prior art everting sleeve devices. Essentially, a cylindrical external casing is provided with a long thin walled plastic tubing which is anchored at one end thereof to the inside wall of the casing and extends along the inside of the casing. The tubing may be open- or closed-ended. By application of external gas pressure between the casing and the tubing, the tubing is forced to turn on itself, or evert, and extend outwardly beyond the end of the casing. Powdered drugs may be applied to the everting surfaces before use and these will be deposited on the mucosa or walls of the body cavity as the tubing extends. If an open-ended tubing is employed, samples of body fluids or the like may be withdrawn through the extended tubing. Withdrawal of the tubing may be effected by withdrawing the tubing in its extended condition or by re-everting the tubing by pulling on an internally mounted withdrawal cord or the like. These prior art devices, while relatively effective, suffer from several serious disadvantages. Firstly, considerable pressure is required to evert the tubing and in the event that the tubing should fail during eversion considerable damage to sensitive and delicate body tissues may result. Secondly, withdrawing an extended tubing from a body cavity may cause considerable friction and hence discomfort or pain to the patient. Everting the extended tubing by means of an internal withdrawal cord or the like is cumbersome and not very practical in the case of very thin long tubes. There is a need, therefore, for an improved everting sleeve device for delivering drugs, absorbents and the like to body cavities, including long narrow body passages, such as, but not limited to, the urethra, bladder, vagina, anus, rectum, and colon in both human and animal patients.

OBJECT OF THE INVENTION

An object of the present invention is to provide an improved everting toroidal low-pressure sleeve device for delivering drugs and the like to internal body cavities or other cavities. Another object of this invention is to provide an everting toroidal sleeve device in combination with an aerosol delivery device for delivery of drugs, absorbents and the like to internal body cavities or other cavities.

Yet another object is to provide novel methods for delivery of pharmaceutical compositions, such as drugs, to internal body cavities, or for absorption of secretions and the like from such cavities.

BRIEF STATEMENT OF THE INVENTION

By one aspect of this invention there is provided an apparatus for delivering a composition to an internal wall or lumen of a cavity, comprising: a housing member having a first open end and a second end; an elongated flexible toroidal member contained within said housing member and having an outer surface portion thereof secured to said housing adjacent said first open end thereof; and means adjacent said second end, contacting a surface portion of said toroidal member, and movable through said housing member towards said first open end thereof so as to cause said toroidal member to evert and extend outwardly from said first open end of said housing member.

By another aspect of this invention there is provided an apparatus for delivering a pharmaceutical or other composition to an internal wall or lumen of a cavity, comprising in combination a housing member having a first open end and a second end; an elongated flexible toroidal member contained within said housing member and having an outer surface portion thereof secured to said housing adjacent said first open end thereof; means adjacent said second end, contacting a surface portion of said toroidal member, and movable through said housing member towards said first open end thereof so as to cause said toroidal member to evert and extend outwardly from said first open end of said housing member; a tubular housing member having a proximal end and an open distal end; a tube contained within said tubular housing having an open distal end and an aerosolized composition delivery chamber at a proximal end thereof; means to extend said tube longitudinally outwardly from said open distal end of said tubular housing and to retract said extended tube back into said tubular housing; and a valve adjacent said delivery chamber to dispense an aerosolized composition contained in said delivery chamber through said tube to said distal end thereof when said tube is extended from said tubular housing member and while it is retracting therein to; wherein said housing member and said toroidal member axially receive said tubular member when in said extended position from said tubular housing member.

By yet another aspect of this invention there is provided an apparatus wherein said means to extend said tube includes a slider cooperating with said tubular housing member to extend said tube longitudinally therefrom.

According to an alternative aspect of this invention, there is provided a method for delivering a pharmaceutical or other composition to an internal wall or lumen of a cavity, comprising: providing a housing member having a first open end and a second end, an elongated flexible toroidal member contained within said housing member and having an outer surface portion thereof secured to said housing adjacent said first open end, and means adjacent said second end, contacting a surface portion of said toroidal member, and movable through said housing member towards said first open end thereof, wherein a selected said composition is disposed on an inner surface of said toroidal member, and advancing said means adjacent said second end through said housing member so as to cause said toroidal member to evert into said internal body cavity and deposit said composition therein.

The cavity may be, but is not necessarily a body cavity such as the urethra, bladder, vagina, anus, rectum, colon, pharynx, nostril, ear canal, or other suitable cavity of a subject in need of drug delivery thereto. The body cavity may also be a non-natural cavity, such as a wound or an infection, or it may be a cavity created during, for example, a surgical procedure. Preferably, the body cavity is the urethra, and more preferably, the adult male or female urethra. Other cavities include inanimate or artificial surfaces su as the inside of tubes, bores, and the like.

BRIEF DESCRIPTION OF THE DRAWINGS

Embodiments of the invention will now be described, by way of example, with reference to the accompanying drawings, wherein.

DETAILED DESCRIPTION OF PREFERRED EMBODIMENTS

Figure 1:
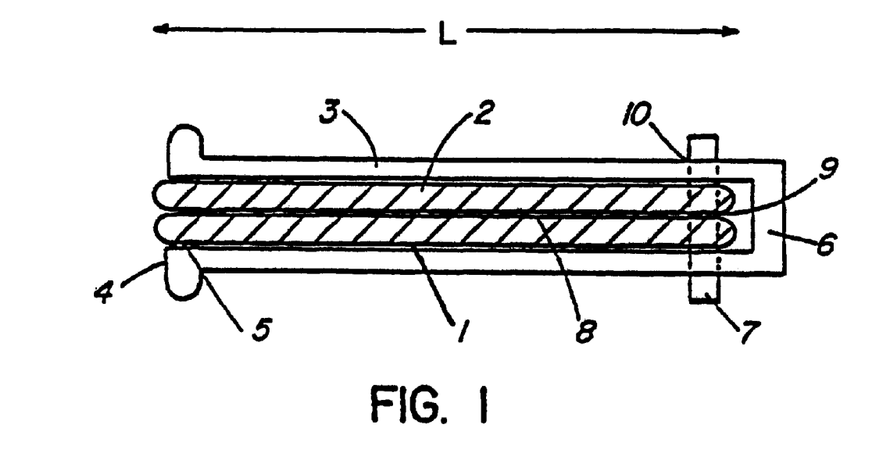
FIG. 1 is a top plan view of a drug delivery device according to one embodiment of this invention, in closed position.

In FIG. 1 there is shown a flexible ring or toroid 1 made from a thin, physiologically inert and acceptable flexible material, about 2 mm to about 25 μm thick, preferably about 0.5 mm to about 50 μm thick, more preferably about 0.25 mm to about 50 μm thick. The toroid is filled with a suitable material 2 which can be physiologically active or physiologically inert, examples of the latter being isotonic, non-isotonic, and saline solutions, water, a polyol such as glycerin, a gas such as nitrogen, a gel, or particulate matter such as beads, under relatively low pressure. The toroid may be made from any plastic, elastomeric or thermoplastic film material, such as silicone, latex, or polyurethane, or it may also be made from a biologically derived material such as, for example, human or animal collagen. The toroid may also be made from woven synthetic or natural material such as Nylon™, cotton, or cellulose. Further, the toroid may comprise a combination of two or more such materials, arranged, for example, in layers. In some applications, such as delivery to the anus or rectum, the film may be thicker in comparison to applications such as delivery to the urethra. It will be appreciated that the thickness selected will depend upon the intended use, so as to provide suitable flexibility and everting/inverting characteristics. It will be further appreciated that the toroid is not rigid and therefore is not a shaft. In yet further applications, the film thickness may be non-uniform, so as to modulate the everting and/or inverting properties of the toroid. In other applications the toroid may be filled with self lubricating solid beads or rings which rotate as the containing surfaces slide over them.

As shown in FIG. 1, the toroid 1 is elongated in one dimension so that it has a length which typically is about 5 to about 40 times the external diameter, but is not limited thereto. Depending on the specific cavity into which the toroid is to be inserted, the diameter D is preferably about 2 to about 30 mm. For example, for delivery of vasodilating drugs to the male or female urethra in cases of sexual dysfunction, the toroid will preferably have an outside diameter in the range of about 6 to about 8 mm, which is the diameter of the adult urethra, and be up to about 30 cm long so that it can be extended beyond the external part of the urethra, or fossa naviculari (in the male) which is composed of squamous epithelium cells and less absorptive, so as to reach the proximal urethra and, in some applications, the bladder. The cross section of the toroid is usually, but not essentially, uniform along its length. Irregular cross sections, e.g., a cross section which changes along the length of the toroid, are also within the scope of this invention. Typically, a toroid having an irregular cross section is constructed such that its cross section is regular when the toroid is inverted, and irregular when the toroid is everted. Irregular cross sections may modulate the everting and/or inverting of toroids, and may facilitate insertion and/or withdrawal from the cavity. Irregular toroids may also be of a shape corresponding to a particular cavity, so as to establish contact with at least a portion of an internal wall of such a cavity when everted therein.

The toroid 1 is mounted inside a housing or applicator 3 and secured at an open end 4 thereof by means of an adhesive 5 or the like. The housing 3 is usually, but not necessarily, a cylindrical or other regularly shaped tube in cross section. At the other, preferably closed, end 6 of the housing 3, a slider 7 is secured to the inner diameter or internal lumen 8 of the toroid 1 by, for example, an adhesive 9. The slider 7 moves along a slot 10 in the housing 3 a distance L.

Figure 3:
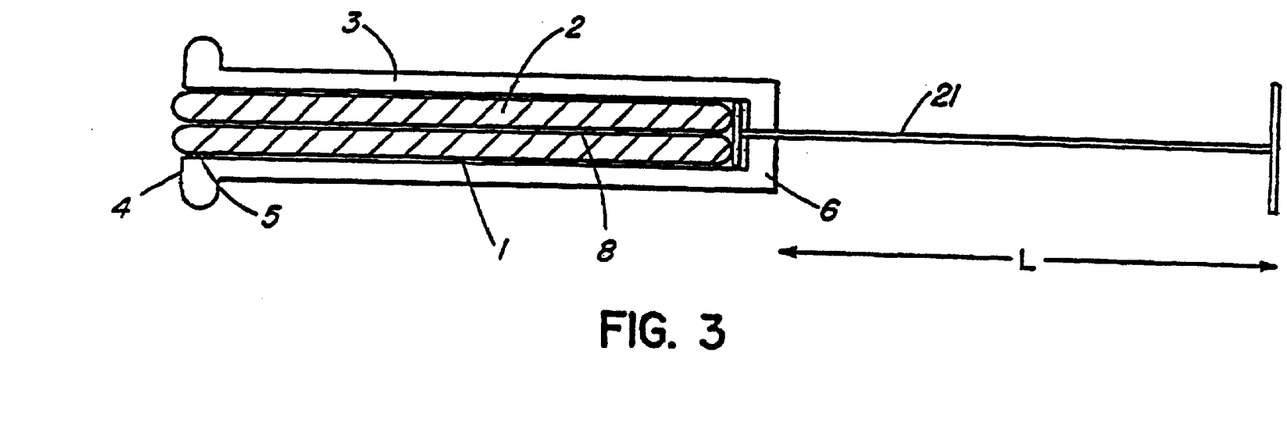
FIG. 3 is a top plan view of an alternative embodiment of the invention, in closed position.
Figure 4:
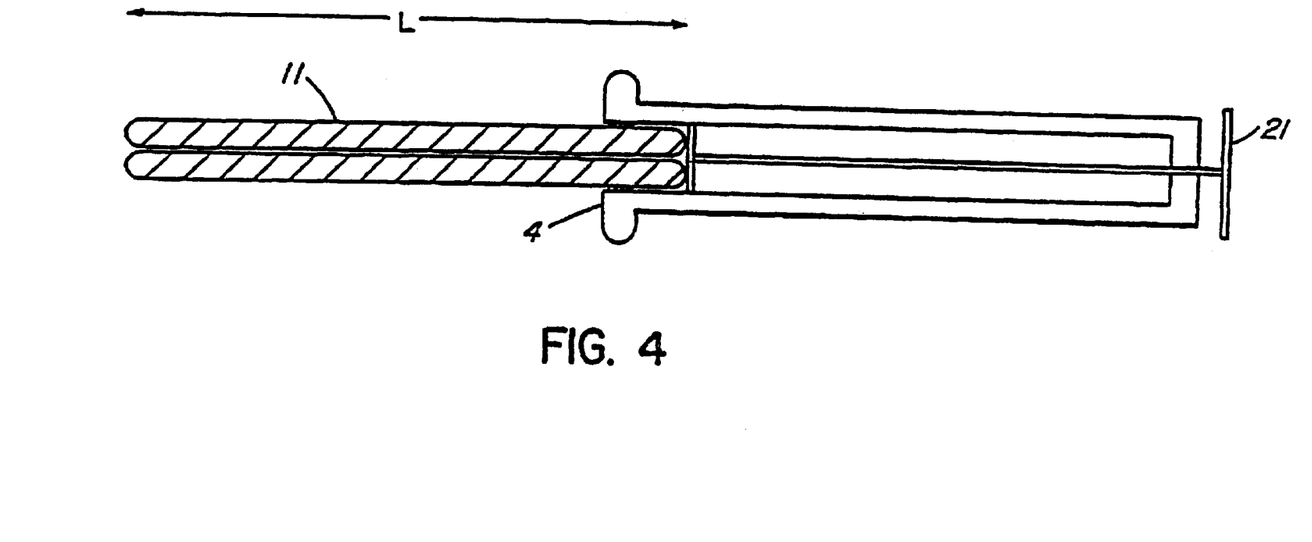
FIG. 4 is a top plan view of the device of FIG. 3 shown in extended position.

In use, the housing 3 is positioned with the end 4 adjacent, for example, the distal urethra, and the slider 7 is moved towards the end 4, thereby causing the toroid to advance in a rolling action into the unopened urethra a distance L/2. The toroid wall 11 that everts from the central lumen 8 to the outside will remain stationary relative to both the housing 3 and the internal wall of the urethra once it is in place. This means that the urethra is opened by lateral pressure only without sliding relative to the mucosa of the urethra, thereby considerably reducing any discomfort to the patient. In an alternative embodiment shown in FIGS. 3 and 4, an external plunger 21 rests against the toroid 1 but is not secured thereto. The plunger may be L to 2L in length. As the plunger is pushed in a distance L, the toroid everts a distance L as well. Withdrawal of the toroid 1 is simply effected by the user moving slider 7 from end 4 towards closed end 6 of housing 3, thereby causing toroid 1 to invert back to the original position as shown in FIG. 1. Again, it is to be noted that there is no sliding motion between the toroid 1 and the urethral mucosa, therefore reducing friction and/or shear forces to a minimum with increased patient comfort, and also ensuring that the deposited drug is not removed from the deposit site.

It will be appreciated that the internal lumen 8 of the toroid, i.e., the everting surface, can be coated before insertion into the cavity with any composition such as one or more drugs or other medicament(s), in any suitable form such as liquid gel, or powder, with or without a carrier therefor, so that, as the toroid everts into the cavity, the composition is delivered to an internal wall or lumen of the cavity. According to the invention, delivery of the composition to an internal wall or lumen of the cavity includes, for example, bringing into contact with an internal wall, or directly depositing onto an internal wall, all or a sufficient quantity of the composition so as to provide the desired efficacy or other desired result. As used herein, the term "interal wall of a cavity" comprises the tissues and secretions associated therewith. For example, in the case of the vagina, the internal wall comprises surface cells of wall tissue and mucosal secretions. The drug or drugs may be salt or base compounds. The drug or drug may be coated on the device as separate components. In some embodiments, such components may be relatively unstable in combination and mix on contact with an internal wall. It will be appreciated that, if desired, the toroid may be everted into the lumen and merely pulled out so that the drug or other compound on the surface of the toroid is sheared off the surface and deposited onto an internal wall of the cavity.

It will also be appreciated that the everting toroid can be used to deliver a depot of a composition, such as a pharmaceutical preparation, into the lumen of a body cavity. The depot may be in the form of, for example, a powder, liquid, or gel, and packaged within a rupturable membrane. In use, the membrane containing the composition is placed at the entrance of the cavity, ahead of the toroid, and advanced into the lumen of the cavity as the toroid is everted. The membrane can be ruptured prior to, during, or upon complete insertion into the cavity. Rupturing of the membrane can be accomplished by any suitable technique known in the art, such as, for example, a string attached to the membrane, passing through the lumen of the toroid, and extending out of the cavity. Alternatively, the membrane enclosing the depot may be a biodegradable or bioerodable membrane, in which case the membrane containing the composition is placed inside the lumen of a cavity using the toroid, and then simply left in place when the toroid is removed from the cavity.

A toroid according to the invention can also be used to collect a sample such as a biological sample from within an internal body cavity. The toroid may be everted and then inserted into a cavity so as to wipe or shear biological material from an internal wall of the cavity, and the toroid then inverted during removal so as to draw out the sample attached to the toroid without shearing it therefrom. Similarly, the toroid may be everted into a cavity, rotated, and then removed by inverting, so that the collected sample remains within the lumen of the toroid. To facilitate collection of a sample the surface of the toroid may be coated with a suitable bioadhesive, and/or provided with suitable roughness, including, for example, ridges, splines, and the like.

Figure 2:
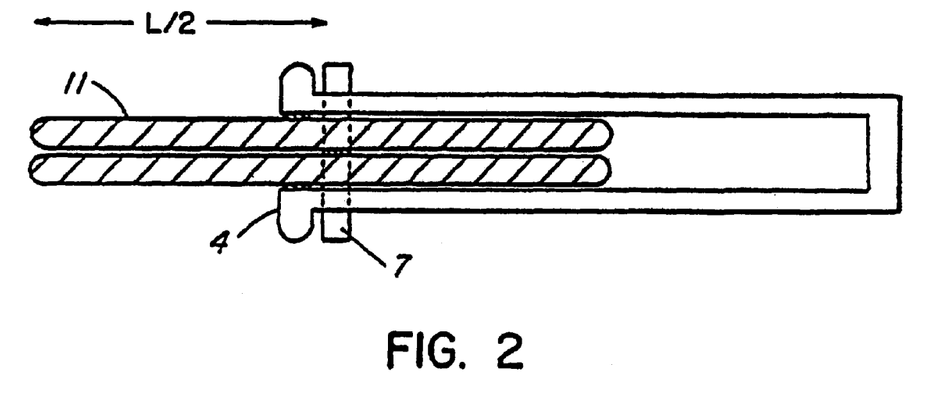
FIG. 2 is a top plan view of the device of FIG. 1 shown in extended position.
Figure 5:
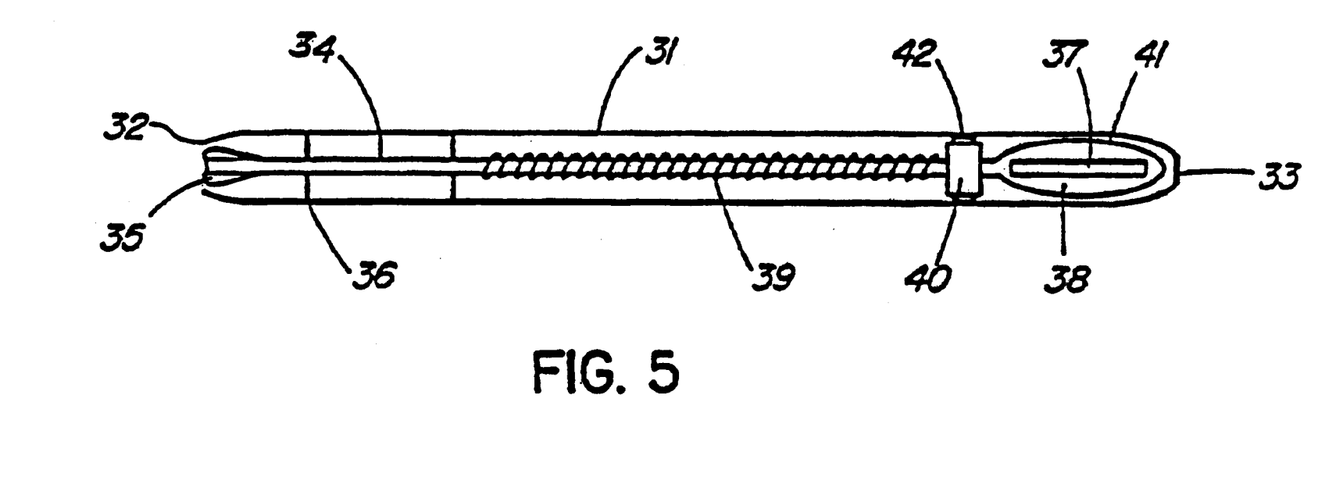
FIG. 5 is a top plan view of an aerosol drug delivery device of the present invention, in closed position.
Figure 6:
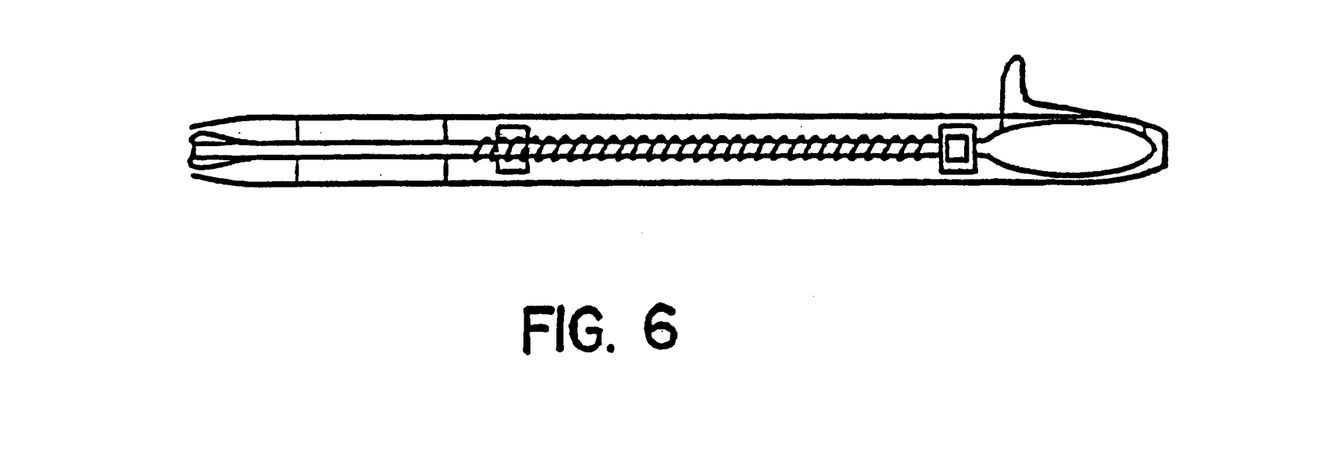
FIG. 6 is a side view of the device of FIG. 5.
Figure 7:
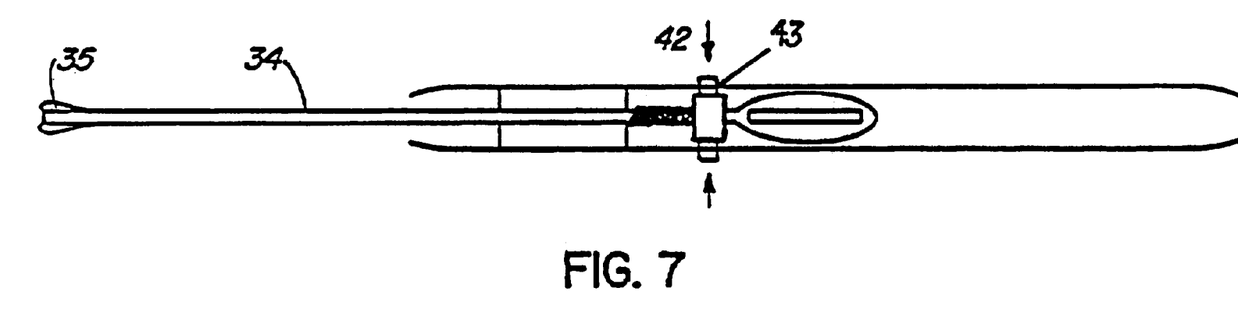
FIG. 7 is a top plan view of the device of FIG. 5, shown in extended position.
Figure 8:
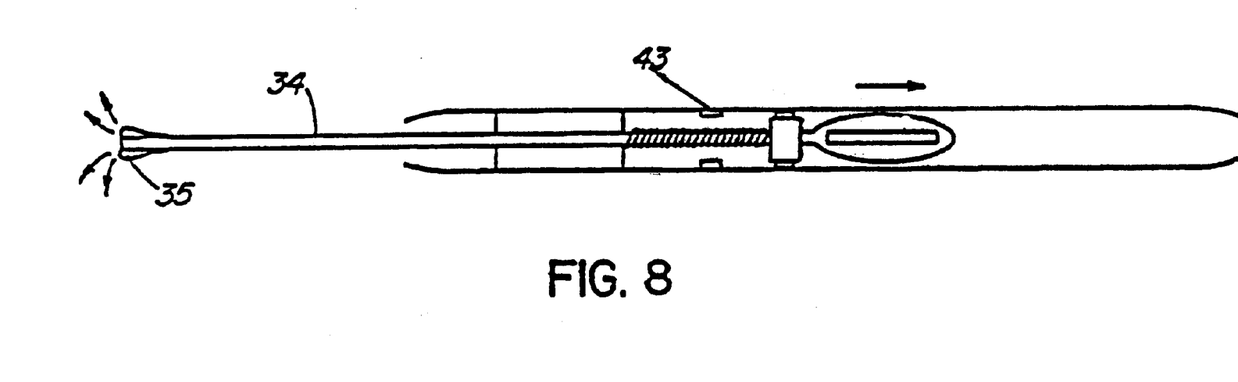
FIG. 8 is a top plan view of the device of FIG. 7 shown during the withdrawal and drug delivery phase of the cycle.
Figure 9:
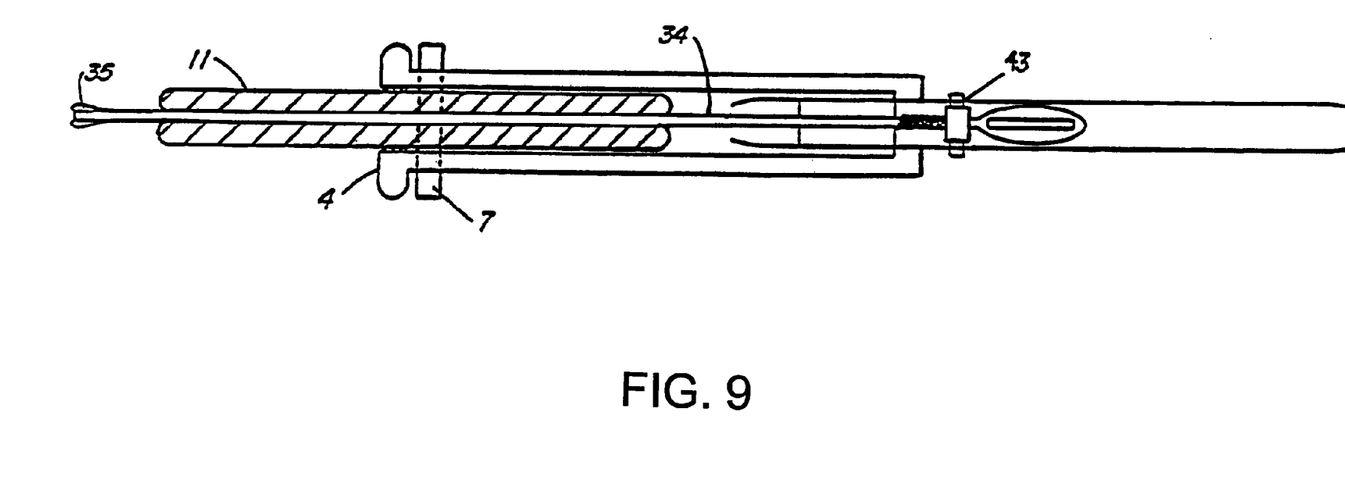
FIG. 9 is a top plan view of an embodiment of the invention wherein the device of FIG. 2 is inserted into the device of FIG. 7.

In accordance with the invention, an aerosol device may be inserted through the extended toroid to deliver compositions to an internal wall or lumen of a cavity, such as the proximal end of the urethra and to the urethral mucosa, as the device is withdrawn. Turning now to FIGS. 5 to 8, there is shown such an aerosol device which may be directly inserted into a body cavity, such as the urethra, but preferably through or with the lumen of an everting toroid such as the everting toroid 1 of FIGS. 1 and 2, as shown in FIG. 9. The everting toroid 1 may have already been inserted into the body cavity, or the toroid and aerosol device may be inserted into the cavity simultaneously (i.e., as a combination). As seen in FIGS. 5 and 6, an elongated tubular housing 31, having an open distal end 32 and a closed proximal end 33 is provided with an aerosol delivery tube or wand 34, preferably made from a rigid but flexible material, such as, for example, a thermoplastic material, having a lubricated glider 35 at the distal end 32 thereof The glider 35 facilitates entry of the flexible aerosol delivery tube or wand 34 into the selected body cavity or into the toroid 1 and eases passage centrally therethrough. The tubular housing 31 is provided with plastic guides 36 which ensure the aerosol delivery tube 34 remains centred therein. A slider 37 is provided adjacent proximal end 33 and an aerosolgas chamber 41 containing an aerosolized drug, to facilitate sliding tube 34 out of distal end 32 of the tubular housing 31, as seen in FIG. 7. The slider 37 slides in a groove 38 in the housing 31. As tube 34 advances from end 32, a spring 39 is compressed between guide 36 and aerosol release valve 40. When tube 34 is fully advanced, as seen in FIG. 7, a spring-loaded release valve button 42 is pushed radially outwardly through an appropriately located opening 43 in housing 31, as seen in FIG. 7. Upon depressing button 42, valve 40 opens and starts to release the aerosolized drug contained in chamber 41 through the tip 35 of tube 34. At the same time, button 42 is again internalized within housing 31 and is moved towards proximal end 33 thereof as compressed spring 39 extends, as seen in FIG. 8. It will be appreciated that the aerosolized drug is ejected directly into the lumen of the cavity and/or onto the internal walls of the cavity as the tip 35 is withdrawn, thereby painting the drug in a relatively uniform manner onto the walls, for direct assimilation without any physical contact with the withdrawing tube 34 and/or toroid 1. Preferably the drug is in the form of a base compound or salt, and more preferably without a solid or liquid carrier. Solid drug may be dissolved in a non-CFC propellant such as, for example, Dymel™ 134A produced by DuPont, such that the propellant becomes a gas upon expansion during delivery to the cavity. It will also be appreciated that when the aerosol device is used in combination with the toroid 1, the toroid 1 must also be withdrawn from the body cavity either together with tube 34 or in advance thereof Preferably, tube 34 is provided with at least one longitudinally extending groove (not shown) along the outer surface thereof to allow venting of aerosol gases and prevent gas pressure build-up within the body cavity. Other venting devices will be apparent to those skilled in the art.

Alternative devices for advancing and retracting the toroid and/or aerosol tube based on hydraulic, electronic or mechanical principles will be apparent to those skilled in the art. For example, a gear drive and stepper motor housed in a casing could easily be used. A simple piston device is also contemplated. Embodiments employing such alternatives are considered to be within the scope of the invention and are covered by the appended claims.

Thus far this invention has been described with reference to physiologically active compositions such as pharmaceutical compositions or the like adhered to the outer surface of the toroidal member. However, it will be appreciated by those of skill in the art that a composition, such as a medicament, absorbent, adsorbent, perfume, or antibacterial compound may be contained on an impermeable membrane forming the toroid. It will also be appreciated by those of skill in the art that a composition, such as a medicament, absorbent, adsorbent, perfume, or antibacterial compound may be contained within and/or on a membrane of selected permeability forming the everting toroid. When the toroid has a selected permeability, a physiologically active composition, for example, can be included with the physiologically inert material for delivery to an internal wall of a cavity when inserted into and left in the cavity for a period of time. A membrane of selected permeability will have a pore size selected to allow particles, e.g., molecules, of one or more compositions or biological substances, e.g., secretions, to pass therethrough at a selected rate or to a selected extent. The toroid can also be used as a tampon for insertion into the vagina, in which case it may contain water-absorbing beads, and possibly, other beads which release, for example, a perfume or antibacterial agent upon contact with water or bodily fluids passing into the tampon through a permeable membrane thereof. In general, the membrane of the toroid may be impregnated or coated, or have a transfer medium with an active compound or any other compound as desired for transport and/or deposit.

We claim:

1. An apparatus for delivering a composition to an internal wall or lumen of a cavity, comprising: a housing member having a first open end and a second end; an elongated flexible toroidal member contained within said housing member and having an outer surface portion thereof secured to said housing adjacent said first open end; and means, adjacent said second end, contacting a surface portion of said toroidal member, and movable through said housing member towards said first open end thereof so as to cause said toroidal member to evert and extend outwardly from said first open end of said housing member, wherein said toroidal member is a tampon comprising a permeable film and an absorbent material contained within said permeable film.

2. The apparatus of claim 1 wherein said tampon further contains at least one of a perfume and an antibacterial agent within said permeable film.

3. The apparatus of claim 1 wherein said composition is impregnated in or coated on said permeable film.

4. An apparatus for delivering a pharmaceutical or other composition in fluid or solid form to an internal wall or lumen of a cavity, comprising in combination a housing member having a first open end and a second end; an elongated flexible toroidal member contained within said housing member and having an outer surface portion thereof secured to said housing adjacent said first open end thereof; means adjacent said second end, contacting a surface portion of said toroidal member, and movable through said housing member towards said first open end thereof so as to cause said toroidal member to evert and extend outwardly from said first open end of said housing member; a tubular housing having a proximal end and an open distal end; a delivery tube adapted to axially fit within said tubular housing and to axially fit within the toroidal member, the delivery tube having an open distal end and a proximal end: an aerosolized composition delivery chamber at said proximal end of the delivery tube; means to extend said delivery tube longitudinally outwardly from said open distal end of said tubular housing and to retract said extended delivery tube back into said tubular housing; and a valve adjacent said delivery chamber to dispense an aerosolized composition contained in said delivery chamber through said delivery tube to said distal end thereof when said delivery tube is extended from said tubular housing and is retracting thereinto.

5. The apparatus of claim 4 wherein said means to extend said delivery tube includes a spring coaxially mounted around said delivery tube for retracting said delivery tube into said tubular housing.

6. The apparatus of claim 5 wherein said means to extend said delivery tube includes a slider cooperating with said tubular housing to extend said delivery tube longitudinally therefrom.

7. The apparatus of claim 4, further comprising a vent for allowing aerosol gas to escape from said body cavity.

8. The apparatus of claim 7, wherein the vent is a longitudinal groove along the outer surface of said housing member.

9. The apparatus of claim 4, wherein the pharmaceutical or other composition is provided without a solid or liquid carrier.

10. The apparatus of claim 4, wherein the pharmaceutical or other composition is dissolved in a non-CFC propellant.

11. A method for delivering a pharmaceutical or other composition in fluid or solid form to an internal wall or lumen of a cavity, comprising:

providing in combination a housing member having a first open end and a second end; an elongated flexible toroidal member contained within said housing member and having an outer surface portion thereof secured to said housing adjacent said first open end thereof; means adjacent said second end, contacting a surface portion of said toroidal member, and movable through said housing member towards said first open end thereof so as to cause said toroidal member to evert and extend outwardly from said first open end of said housing member; a tubular housing having a proximal end and an open distal end; a delivery tube adapted to axially fit within said tubular housing and to axially fit within the toroidal member, the delivery tube having an open distal end and a proximal end; an aerosolized composition delivery chamber at said proximal end of the delivery tube; means to extend said delivery tube longitudinally outwardly from said open distal end of said tubular housing and to retract said extended delivery tube back into said tubular housing; and a valve adjacent said delivery chamber to dispense an aerosolized composition contained in said delivery chamber through said delivery tube to said distal end thereof when said delivery tube is extended from said tubular housing member and is retracting thereinto;

advancing said means adjacent said second end through said housing member so as to evert said toroidal member into said internal body cavity;

inserting and extending said delivery tube through said toroidal member; and operating said valve when said delivery tube is extended so as to release said composition into said internal body cavity.

12. The method of claim 11, further comprising providing a vent for allowing aerosol gas to escape from said body cavity.

13. The method of claim 12, wherein the vent is a longitudinal groove along the outer surface of said housing member.

14. The method of claim 11, wherein the pharmaceutical or other composition is provided without a solid or liquid carrier.

15. The method of claim 11, wherein the pharmaceutical or other composition is dissolved in a non-CFC propellant.

16. A method for delivering a pharmaceutical or other composition in fluid or solid form to an internal wall or lumen of a cavity, comprising:

providing in combination a housing member having a first open end and a second end; an elongated flexible toroidal member contained within said housing member and having an outer surface portion thereof secured to said housing adjacent said first open end thereof; means adjacent said second end, contacting a surface portion of said toroidal member, and movable through said housing member towards said first open end thereof so as to cause said toroidal member to evert and extend outwardly from said first open end of said housing member; a tubular housing having a proximal end and an open distal end; a delivery tube adapted to axially fit within said tubular housing and to axially fit within the toroidal member, the delivery tube having an open distal end and a proximal end; an aerosolized composition delivery chamber at said proximal end of the delivery tube; means to extend said delivery tube longitudinally outwardly from said open distal end of said tubular housing and to retract said extended delivery tube back into said tubular housing; and a valve adjacent said delivery chamber to dispense an aerosolized composition contained in said delivery chamber through said delivery tube to said distal end thereof when said delivery tube is extended from said tubular housing member and is retracting thereinto;

extending said delivery tube through said toroidal member;

advancing said means adjacent said second end through said housing member so as to evert said toroidal member into said internal body cavity and simultaneously insert said delivery tube into said internal body cavity;

operating said valve when the delivery tube is extended so as to release said composition into said internal body cavity.

17. The method of claim 16, further comprising providing a vent for allowing aerosol gas to escape from said body cavity.

18. The method of claim 17, wherein the vent is a longitudinal groove along the outer surface of said housing member.

19. The method of claim 16, wherein the pharmaceutical or other composition is provided without a solid or liquid carrier.

20. The apparatus of claim 16, wherein the pharmaceutical or other composition is dissolved in a non-CFC propellant.

* * * * *